United States Patent [19]
McLeod

[11] Patent Number: 5,376,245
[45] Date of Patent: * Dec. 27, 1994

[54] PORTABLE MAGNETIC FIELD ANALYZER FOR SENSING ION SPECIFIC RESONANT MAGNETIC FIELDS

[75] Inventor: Bruce R. McLeod, Bozeman, Mont.

[73] Assignee: Life Resonances, Inc., Bozeman, Mont.

[*] Notice: The portion of the term of this patent subsequent to May 31, 2011 has been disclaimed.

[21] Appl. No.: 145,381

[22] Filed: Oct. 28, 1993

Related U.S. Application Data

[63] Continuation-in-part of Ser. No. 899,490, Jun. 16, 1992, Pat. No. 5,316,634.

[51] Int. Cl.$^5$ .................. B65D 85/18; G01R 33/022
[52] U.S. Cl. ........................... 204/155; 204/299 R; 606/13; 324/260; 324/247
[58] Field of Search ............ 324/260, 247, 261; 204/299 R, 155; 606/13

[56] References Cited

U.S. PATENT DOCUMENTS

| | | | |
|---|---|---|---|
| 4,818,697 | 4/1989 | Liboff et al. | 435/173 |
| 4,932,951 | 6/1990 | Liboff et al. | 606/13 |
| 5,045,050 | 9/1991 | Liboff et al. | 600/9 |
| 5,059,298 | 10/1991 | Liboff | 204/299 |
| 5,067,940 | 11/1991 | Liboff et al. | 600/13 |
| 5,077,934 | 1/1992 | Liboff et al. | 47/1.3 |
| 5,087,336 | 2/1992 | Liboff et al. | 204/155 |
| 5,088,976 | 2/1992 | Liboff et al. | 600/13 |
| 5,100,373 | 3/1992 | Liboff et al. | 600/13 |
| 5,106,362 | 4/1992 | Liboff et al. | 600/13 |

*Primary Examiner*—John Niebling
*Assistant Examiner*—Arun S. Phasge
*Attorney, Agent, or Firm*—Dykema Gossett

[57] ABSTRACT

A portable magnetic field analyzer for sensing ion specific resonant magnetic fields. The analyzer has a magnetometer which measures the magnetic field produced by both ac and dc sources along an axis and determines the dc field plus the fundamental and various harmonic frequencies. A microcontroller uses this information to calculate various cyclotron resonance frequencies and then compares the calculations to stored data relating to cyclotron resonance frequencies of certain biologically important ions such as calcium, potassium and magnesium. A display notifies the user when resonance conditions (within a set tolerance) exist.

20 Claims, 6 Drawing Sheets

PORTABLE MAGNETIC FIELD ANALYZER FOR SENSING ION SPECIFIC RESONANT MAGNETIC FIELDS

This is a continuation-in-part of application Ser. No. 07/899,490 filed Jun. 16, 1992, the entire disclosure of which is incorporated herein by reference, now U.S. Pat. No. 5,316,634.

FIELD OF THE INVENTION

The present invention relates generally to the interaction of magnetic fields and biological systems. More specifically, the present invention provides a novel method and apparatus for assessing the risk of magnetically-induced biological changes which may occur due to the presence of specific magnetic resonance conditions in the home or work place. The magnetic field analyzer of the present invention determines the directions and magnitudes of ac and dc magnetic fields at any point where a reading is taken, including the dc geomagnetic field and ac fields from sources such as power transmission lines. Through a series of calculations involving ac field frequency (both fundamental and harmonic frequencies), combined ac and dc field strengths and magnetic resonance conditions of certain biologically important ions (based on the charge-to-mass ratio of the ions), the magnetic field analyzer of the present invention automatically determines whether the test area is subject to biologically significant and possibly dilatorious magnetic fields.

BACKGROUND OF THE INVENTION

It has been known for many years that magnetic fields can influence biological processes. For example, in the article "Time-Varying Magnetic Fields: Effect on DNA Synthesis" *Science* 223:818–820 (1984), a correlation between DNA synthesis and time varying magnetic fields is shown. In the article "Effects of ELF (1–120 Hz) and Modulated (50 Hz) RF Fields on the Efflux of Calcium Ions From Brain Tissue In Vitro", *Bioelectromagnetics* 6:1–11 (1985), Blackman reports that calcium efflux from cerebral tissue can be increased by exposing the tissue to an electromagnetic field.

In addition, a number of devices and methodologies have been developed for the treatment of various medical conditions which rely on the application of specific magnetic fields to a biological subject or target tissue of a patient. For example, in U.S. Pat. No. 4,932,951 entitled "Method and Apparatus for Controlling Tissue Growth With an Applied Fluctuating Magnetic Field" the use of an applied magnetic field which combines with the existing geomagnetic field is described for regulating tissue growth. In U.S. Pat. No. 4,818,697, "Techniques for Enhancing the Permeability of Ions Through Membranes" and U.S. Pat. No. 5,059,298 entitled "Method and Apparatus for Regulating Transmembrane Ion Movement", there are described methods and apparatus for applying magnetic fields to biological systems based on achieving resonance states for ions such as calcium, magnesium and potassium. The specific resonances described therein are a function of the charge-to-mass ratios of the ions. The role of cyclotron resonance frequencies in transmembrane ion movement of selected ions through applied magnetic fields is also disclosed. In U.S. Pat. No. 5,087,336 entitled "Methods and Apparatus for Regulating Transmembrane Ion Movement Utilizing Selective Harmonic Frequencies and Simultaneous Multiple Ion Regulation", the interplay of harmonic frequencies and cyclotron resonance is also described.

Most recently research has been conducted on the question of whether there are health risks associated with electromagnetic fields produced from electric current-carrying devices such as power transmission lines, distribution lines, or even house wiring and grounding systems. Some researchers believe that a strong correlation exists between the incidence of certain diseases and the subject's proximity to sources of electromagnetic fields. For example, D. A. Savitz and E. E. Calle, in their study entitled "Leukemia and Occupational Exposure to Electromagnetic Fields: Review of Epidemiological Surveys", *Journal of Occupational Medicine* 29:47–51 (1987), present data suggesting an increased risk of leukemia among men with occupational exposure to 60 hertz (60 Hz) type electromagnetic fields. Additionally, R. S. Lynn, P. C. Dischinger, J. Conde, and K. P. Farrell have found that 60 Hz electromagnetic field exposure may promote brain tumors. These findings are presented in the article entitled "Electromagnetic Fields and the Occurrence of Brain Tumors: An Analysis of Possible Associations", *Journal of Occupational Medicine* 27:413–415 (1985). There are a number of theories which have been advanced in an effort to explain the apparent correlation between 60 Hz electromagnetic fields and perceived health risks and the issue is the subject of much debate.

It is also known that a number of portable devices are available which sense magnetic fields and which provide a readout of the field parameters. None of these prior art devices, however, provide a portable device which determines the magnitudes and directions of dc with respect to a known direction such as due north (including the geomagnetic field) and ac magnetic fields along three perpendicular axes, calculates specific field values which are automatically compared to a second set of values representative of ion resonance values and displays information regarding the presence of a field value near a resonant value which could pose health risks. The present invention addresses this need.

SUMMARY OF THE INVENTION

In accordance with the present invention there is provided in one aspect a magnetic field analyzer comprising a portable device which measures magnetic fields in an area along three perpendicular axes. The three resultant signals are digitized and processed via Fast Fourier Transform (FFT). The magnetic field strength or flux density (of the ac and of the dc field) along each axis is measured which is generally the sum of the ac field and the geomagnetic field, although in some instances local non-geomagnetic dc sources may be present. The ac field will consist of any local source of such fields, for example power transmission lines. These data, along with the fundamental frequency of the ac field along each axis and several harmonics of this frequency, are analyzed by a microcontroller in the device. In the analysis, the component of the dc field that is in the direction of the ac magnetic field is defined and may be used for further calculations in the microcontroller to determine whether any field alone the axis is in resonance with a biologically significant ion. It is to be understood that in the present invention the ac component and the dc component are measured independently. In one embodiment, only the strongest of the three measured fields (x, y, or z) is analyzed.

Resonance is determined with reference to the charge-to-mass ratio of the biologically significant ions as a function of the equation $F_c/B = q/(2\pi n)$, where, for a given axis, $F_c$ is the frequency of the alternating component of the measured magnetic field, B is the value of the flux density of the calculated component of the measured dc field that is parallel to the ac magnetic field in Tesla, and $q/m$ is the charge-to-mass ratio of a preselected ion in Coulombs per kilogram. Accordingly, it will be appreciated that the calculated dc component is the component parallel to the ac magnetic field. In essence, the microcontroller, based on the value of B and the charge-to-mass ratio of selected biologically important ions, determines specific resonant frequency values against which the measured fundamental frequency and harmonic frequencies of the measured frequency (determined using the Fast Fourier Transform) are compared to determine whether a potentially hazardous magnetic field exists along an axis. Harmonic frequencies at the measured value of B are in effect determined for the selected ions, preferably the third, fifth, and fifteenth harmonics. Both the fundamental and the 15 largest (lowest) harmonics of the measured field along each axis are also determined. Thus, this results in an evaluation of the measured fields and a number of their harmonics with the fundamental ion resonance states and selected harmonic resonance states for several ions.

Where a measured field value is in close proximity to the resonance value for a significant ion, for example within ±5%, information regarding the existence of resonance and, where desired, the measured value, the resonant ion identity and percent deviation, are displayed on the device readout. Since it has been demonstrated in the past that the magnitude of transmembrane ion movement of various ions can be correlated to a number of discreet biological phenomenon, ion identification may provide useful information in addition to establishing the existence of resonant fields.

To provide repeatability and comparativeness of the results of different measurements, it is also proposed to conduct the measurements with preliminary spatial and magnetic orientation of the device.

Further objects, features and advantages of the invention will become apparent from the consideration of the following description and claims, when taken in conjunction with the accompanying drawings.

BRIEF DESCRIPTION OF THE DRAWINGS

Various advantages of the present invention will become apparent to those skilled in the art by reading the following specification and by reference of the following drawings in which.

DETAILED DESCRIPTION OF THE PREFERRED EMBODIMENTS

Figure 1:
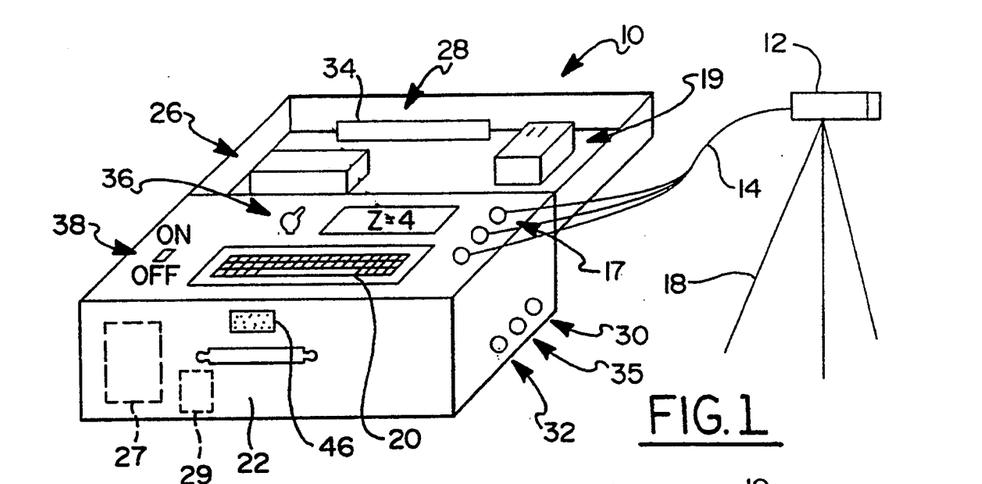
FIG. 1 is a perspective view of the magnetic field analyzer in one embodiment of this invention.

Referring first to FIG. 1 of the drawings, magnetic field analyzer 10 in one embodiment is shown generally having magnetometer sensing head 12 attached at one end by cable 14 to carrying case 22 via BNC connectors 17. Magnetometer sensing head 12 preferably comprises a magnetometer unit which includes compensation circuitry that enables it to output accurate magnetic field measurements for fields with any frequency between 0 to 1,000 Hertz and with a field magnitude between ±1.0 Gauss maximum. Magnetometer sensing head 12 is preferably a flux gate sensing head. Output from magnetometer sensing head 12 is preferably in the form of 3 analog signals which are in the linear relation, one volt to (0.1) Gauss. These signals are transmitted via cable 14.

Figure 10:
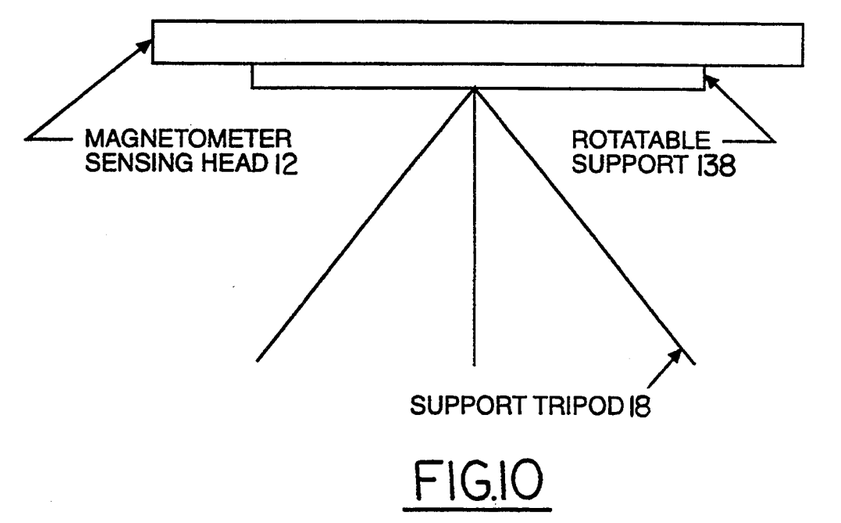
FIG. 10 illustrates a disposition of the sensing part of the analyzer with respect to magnetic field measurements in the present invention.
Figure 11:
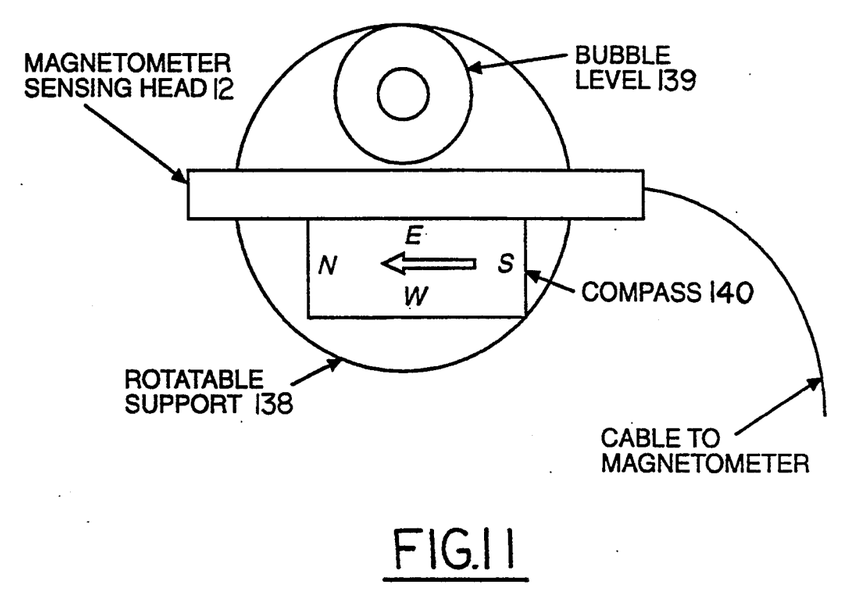
FIG. 11 illustrates a top view of the sensing part of the analyzer shown in FIG. 9, in another embodiment of the invention.

Sensing head 12 is shown mounted on non-magnetic tripod 18 to assure repeatability of location and orientation and comparativeness of measurements. As it can be seen in more details in FIGS. 10 and 11, the magnetometer sensing head 12 is mounted on a flat rotatable support 138 that is adjusted to level, with the aid, for example, of a bubble level 139 built into the support 138, before each measurement. There might be provided another surface (not shown) upon which the above support rotates and which, in turn, is mounted on height tripod 18. The tripod 18 is made adjustable, and for any reading, the sensing head 12 is set at a desired height (such as one meter), then leveled, and then rotated so that the head 12 is along a north-south line. Using N-S coordinates is arbitrary but convenient to remember. The north-south line is established by use of a compass 140 that is also built into the flat rotatable support 138. The result of spatial and magnetic orientation of sensing head 12 is that the measurement can be repeated in exactly the same position and height at a later date. Moreover, data can be obtained that can be quantified and compared to similar data taken at other points in the area or, for that matter, in areas far removed.

An ac converter 19, alpha-numeric keyboard 20, liquid crystal display 34, magnetic sensor power supply 26, microcontroller 29 and microcontroller power supply 27 are all mounted in fiberglass carrying case 22. Analyzer 10 is also equipped with various cables, fuses 30, 32 and liquid crystal display 34. External power may be supplied via connector 35 or an on-board power supply for the microcontroller and associated devices may be provided. A single power supply for analyzer 10 is most preferred. LCD contrast knob 36 and on/off switch 38 are also shown.

Figure 8:
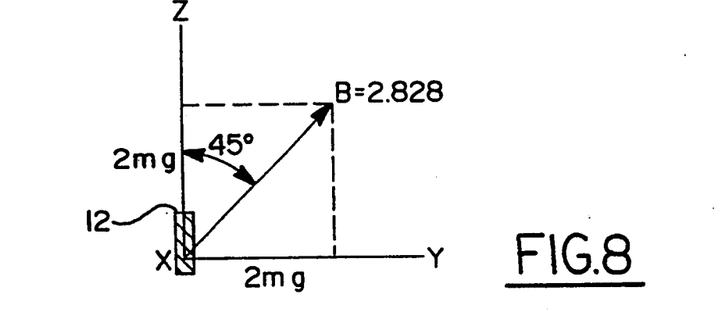
FIG. 8 illustrates an x, y, z coordinate system with respect to magnetic field measurements in the present invention.

It should be realized by one of ordinary skill in the art that sensing head 12 can be placed at any arbitrary angle with respect to any arbitrary axis, while still accurately sensing or "reading" the magnetic field strength. For example, if head 12 were placed along a the "z" axis of a conventional "x", "y" and "z" coordinate system (as illustrated in FIG. 8) and if head 12 measured 2 milligauss along the "z" and "y" axis and 0 milligauss along the "x" axis, one of ordinary skill in the art would recognize that the magnetic field has a magnitude of 2.828 milligauss since the magnetic field magnitude is equal to $((2)^2+(2)^2+0)^{\frac{1}{2}}$.

Figure 9:
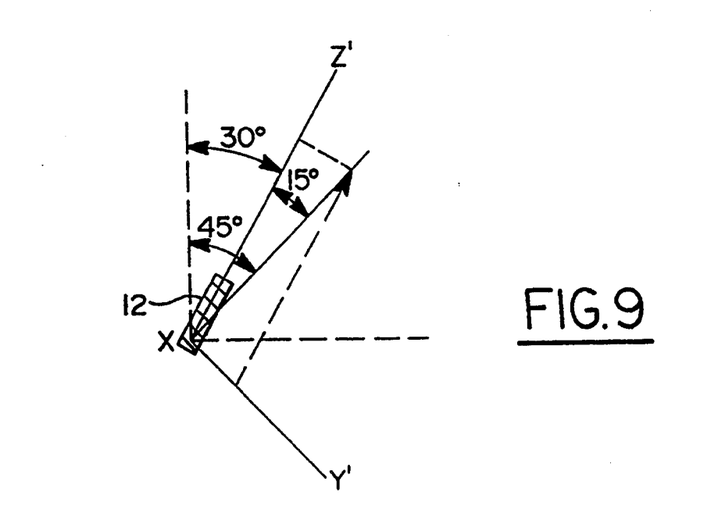
FIG. 9 illustrates an x, y, z coordinate system with respect to magnetic field measurements in the present invention.

If head 12 were rotated by 30° about the "x" axis (as shown in FIG. 9), the head would sense a field of 2.732 milligauss along the "z" axis, 0 along the "x" axis, and 0.732 milligauss along the "y" axis. Accordingly, the magnitude is still 2.828. Moreover since tripod 18 is adapted to fix head 12 in a known and selectable position for all readings, we get information or readings associated with directions and points defined by the angles "$\phi$" and "$\Theta$" (respectively representing an angle from the "x" axis and the angle from the "z" axis).

By use of this information, one of ordinary skill in the art can calculate the position of the measured magnetic field by use of the standard axis arrangement shown above. In the preferred embodiment of this invention, the "x" axis is chosen in the preferred embodiment along the north-south line, with North being taken as the +x direction. This then defines a fixed x,y,z right handed coordinate system that those of ordinary skill in the art will recognize and be able to use to analyze data.

Figure 2:
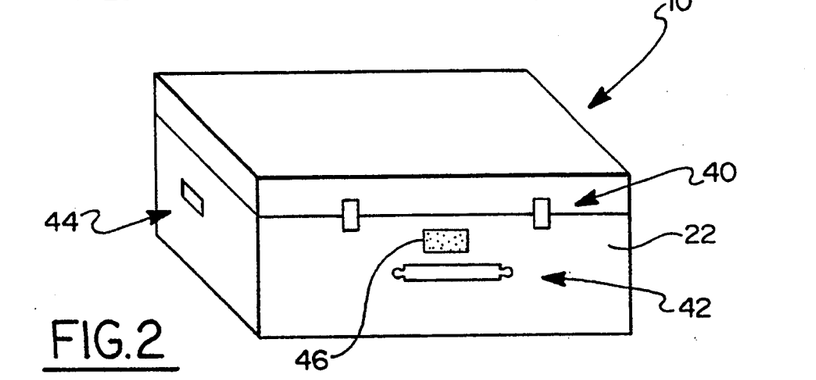
FIG. 2 is another perspective view of the analyzer depicted in FIG. 1.

As seen in FIG. 2, carrying case 22 is also provided with snap fasteners 40, handle 42 and RS-232 port 44 for transferring data to a PC computer (not shown). Audible resonance detection alarm 46 is also provided.

Figure 3:
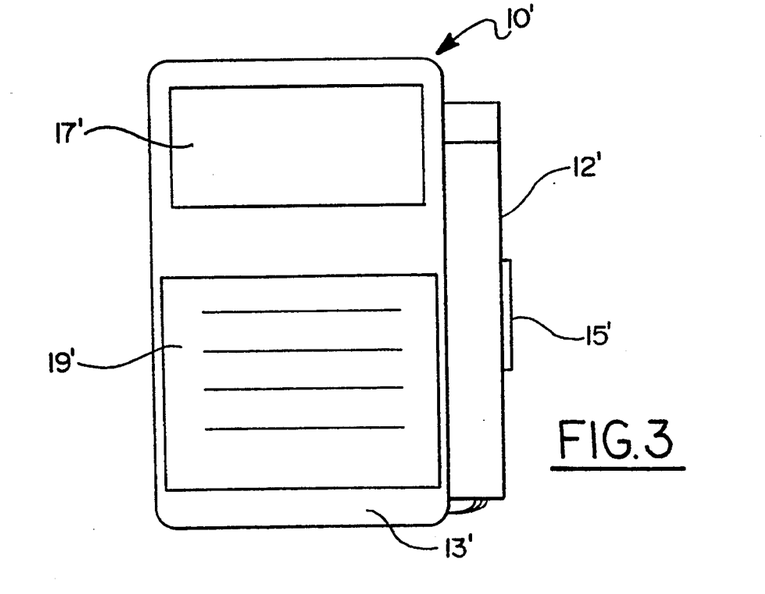
FIG. 3 is a front elevational view of a hand-held embodiment of the magnetic field analyzer of the present invention.

In another embodiment, and referring now to FIG. 3 of the drawings, analyzer 10' is shown as a hand-held device having magnetic sensing head 12' attached to housing 13' via bracket 15'. Housing 13' is equipped with LCD readout 17' and keyboard 19'. In this embodiment, all of the components, in readily available miniaturized form, are carried on-board or attached to housing 13', including the magnetometer, power supply and microcontroller.

Figure 4:
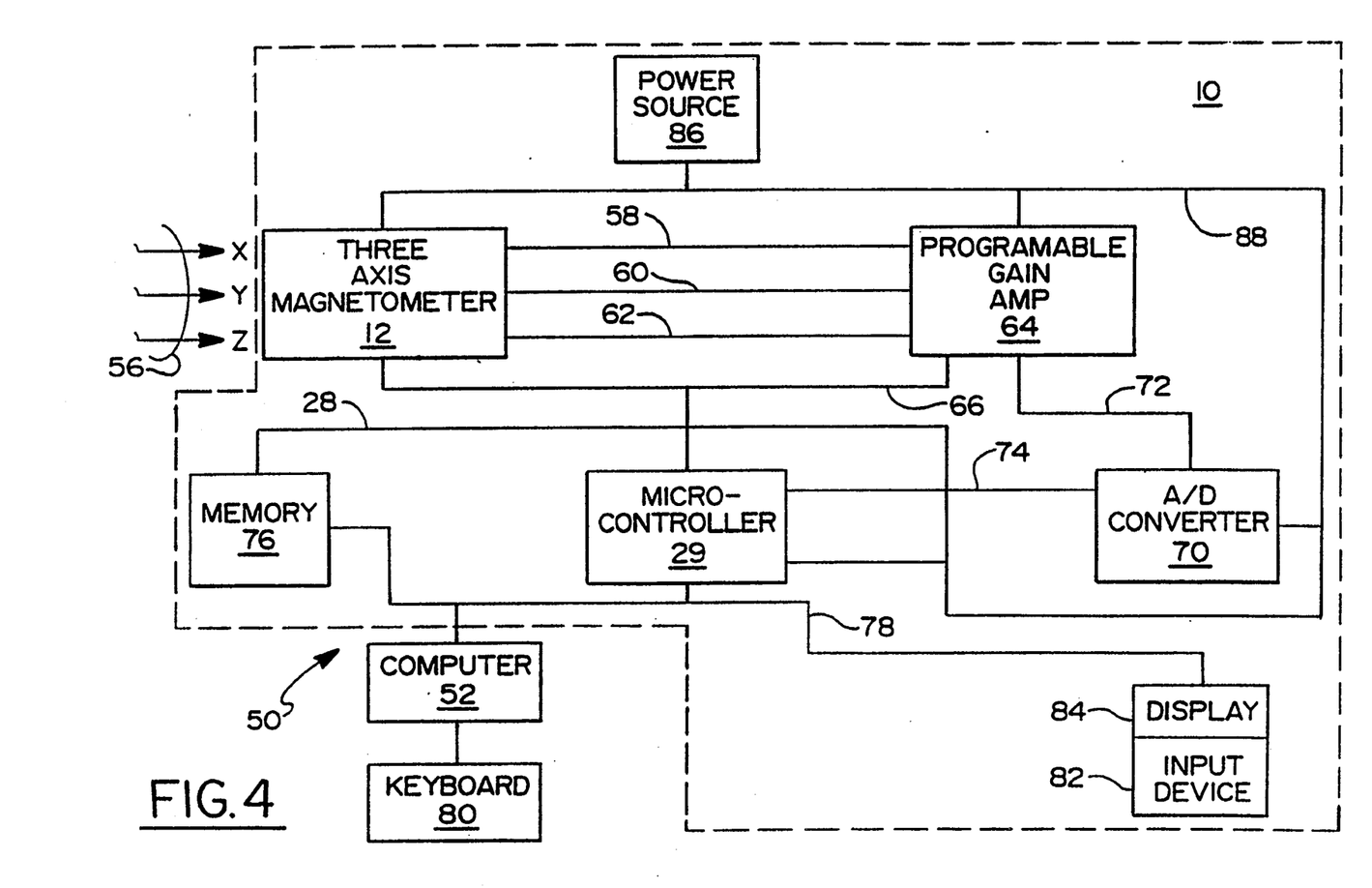
FIG. 4 is a block diagram illustrating the functional elements of the present invention.

Referring now to FIG. 1 and to the schematic of FIG. 4, there is shown a magnetic field analyzer made in accordance with the teachings of the preferred embodiment of this invention. As shown in FIG. 4, analyzer system 50 preferably includes analyzer 10 in communication with PC computer 52 for reasons which will be described more fully hereinafter. Accordingly, a three axis magnetometer 12 is provided, adapted to receive three-dimensional magnetic flux signals or field 56. In the preferred embodiment of this invention, magnetometer 12 comprises a three axis flux gate magnetometer, manufactured by Barrington Instruments Ltd., of London, England, and referenced by Model No. MAG-03MS-100. It should be appreciated by one of ordinary skill in the art that other magnetometers may be used, including a three-axis Hall magnetometer although the Hall device is less desirable. An important aspect of the present invention is the selection of the magnetometer. It is essential that a magnetometer be used which can measure the dc component of the magnetic field in the area to be tested. Thus, for example, a coil-type magnetic field sensor would generally be inappropriate due to its inability to detect the dc magnetic field component. By providing a magnetometer of the preferred type, the geomagnetic field component plus any other dc magnetic field are measured along with the ac magnetic field to determine the static or dc reference level. Thus, it will be appreciated that field 56 comprises the total or sum of magnetic field vectors for both ac and dc magnetic field sources along the X, Y and Z axes, i.e. each axis represents a vector having both dc and ac components. The dc component will include the geomagnetic field as well as any other source of a dc field. The ac component will include such sources as magnetic fields produced by local power transmission lines and the like.

Upon receipt of flux signals 56, magnetometer 12 produces signals on buses 58, 60, and 62, respectively indicative of the amplitude of the flux in the "X", "Y", and "Z" directions or dimensions. These amplitude indicative signals are input to a programmable gain amplifier assembly 64, where the signals are amplified to a level specified by amplification control signals, appearing on bus 66 and generated by microcontroller 29. The amplified amplitude signal is then input to a conventional analog-to-digital converter 70, by means of bus 72. In the preferred embodiment of this invention, analog-to-digital converter 70 comprises a Maxim Model No. 181. Alternatively, these amplitude indicative signals, if digital, could be input to a conventional digital-to-analog converter (not shown). The output of this converter could be input into amplifier 64 and then to converter 70 by means of bus 72. The digital amplitude signal, emanating from converter 70, is placed onto bus 74 and input to microcontroller 29, where it is analyzed in accordance with the operational steps to be discussed. In the preferred embodiment of this invention, microcontroller 29 comprises a Motorola Model No. MC68332PFB microcontroller.

As further shown, assembly 50 also includes a memory portion 76, coupled to microcontroller 29 by means of bus 28. Specifically, memory 76 is adapted to receive a stored program that directs microcontroller 29 to perform certain steps essential to comparing the measured field components to specific ion resonances. Moreover, memory 76 is further adapted to store the predefined and preselected values used within the normal operation of assembly 50. The operational steps and values will be explained more fully hereinafter.

Assembly 50 optionally, but preferably, includes a computer 52 (such as an IBM personal computer "Model AT"), including a conventional keyboard 80. Computer 52 is preferably also coupled to memory 76 and microcontroller 29 by means of bus 78 and, as will be appreciated by one of ordinary skill in the art, may use bus 78 to remotely place a desired operating program into memory 76, and receive measured magnetic field data from controller 29. Moreover, assembly 50 also includes an input 82 and display device 84 coupled to microcontroller 29 and memory 76 by means of bus 78; and a typical power source (shown as a combined power source 86 in FIG. 4) coupled to magnetometer 12, microcontroller 28, converter 70, memory 76, input device 82 and display 84, by means of power bus 88 (not shown to microcontroller 28, memory 76, input device 82 and display 84). It is to be understood that analyzer 10 is the same as system 50, but without computer 52. Device 82 includes keyboard 20. Display 84 includes LCD 34. As will be appreciated by those skilled in the art, computer 52 is adapted, in the preferred embodiment of this invention, to also allow a user to remotely interact with analyzer 10 via port 44 with the use of a modem. Moreover, device 82 and computer 52 are also adapted to allow a user to uniquely identify or "tag" data, stored within memory 76, in order to uniquely associate stored data with a particular date, time, and/or place. Most preferably, the operations of computer 52 are all provided on-board magnetic field analyzer 10 using conventional chip technology and an alphanumeric keypad as input device 82.

Figure 5:
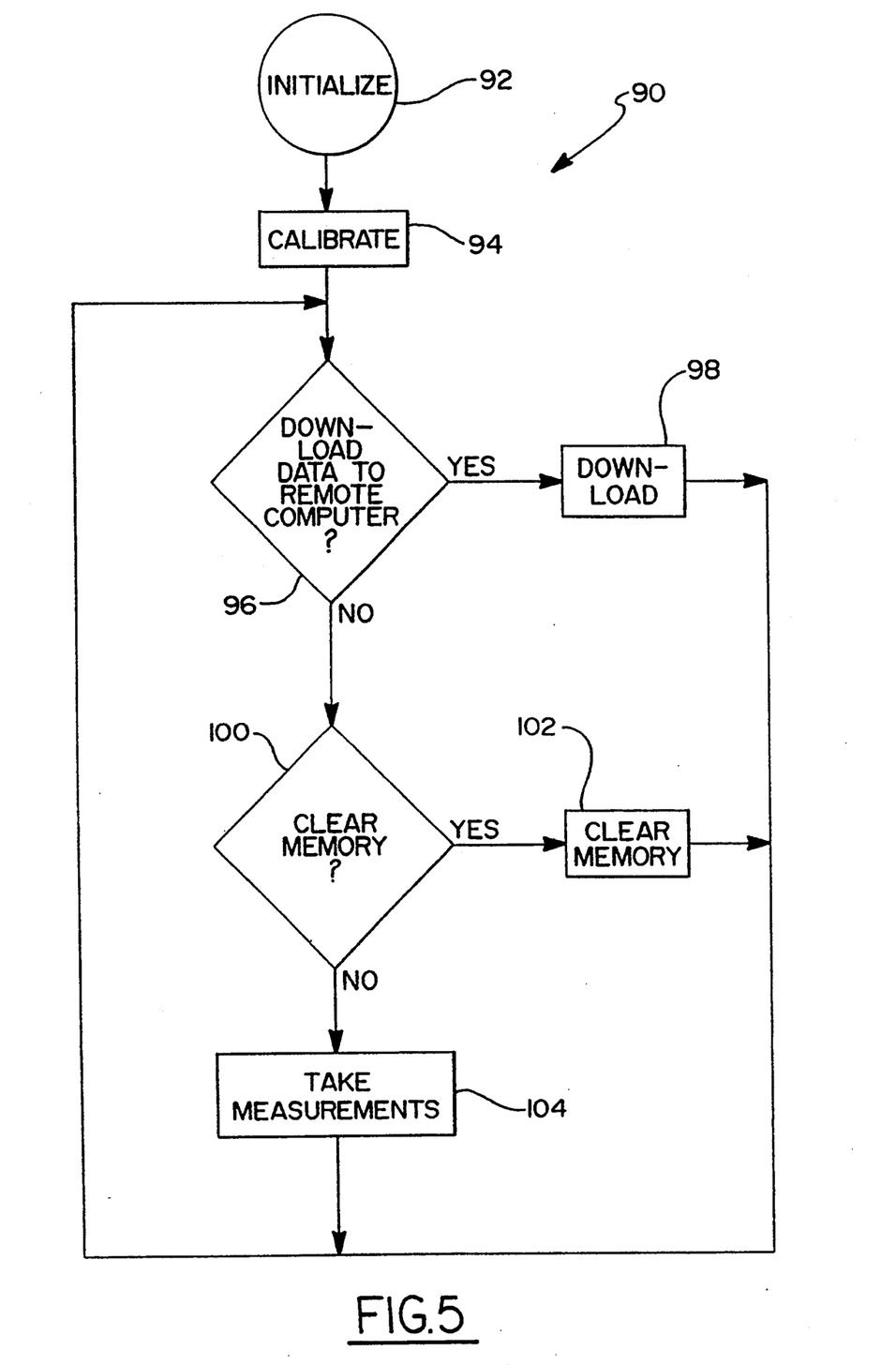
FIG. 5 is a flow chart illustrating the general sequence of operational steps associated with the magnetic field analyzer of FIGS. 1 and 2.

To more fully appreciate and understand the operation of analyzer 10 and assembly 50 according to the preferred embodiment of this invention, reference is now made to flow chart 90 of FIG. 5. As shown, microcontroller 29 performs an initial step 92, during which controller 29 ensures that data reception portions of memory 76 are clear and that electrical power is generated by source 86 adequate to allow assembly 50 to operate. Step 92 is then followed by step 94 in which microcontroller 29 calibrates magnetometer 12 in a conventional manner and further performs conventional "self-test" operations on amplifier 64 and convertor 70 in order to ensure operational integrity of these assembly portions. Step 94 is then followed by step 96 in which microcontroller 29 determines whether data is to be downloaded from memory 76 to computer 52. This download only occurs, in the preferred embodiment of this invention, upon receipt of a command emanating from device 82. If this download is desired, step 96 is followed by step 98, in which data is output from memory 76 to computer 52 for archival storage purposes.

Alternatively, step 96 is followed by step 100 in which microcontroller 29 determines whether a user desires to have memory 76 cleared. If a "memory clear" command has been received from input device 82, microcontroller 29 enters step 102, where it clears or "empties" memory 76. Such "memory clearing" occurs when errors have been created or found in the stored program, or when the memory has been filled to its data storage capacity. Alternatively, step 100 is followed by step 104 in which microcontroller 29 measures the ambient electromagnetic field, for both dc and ac sources, in accordance with the preferred embodiment of this invention.

Figure 6:
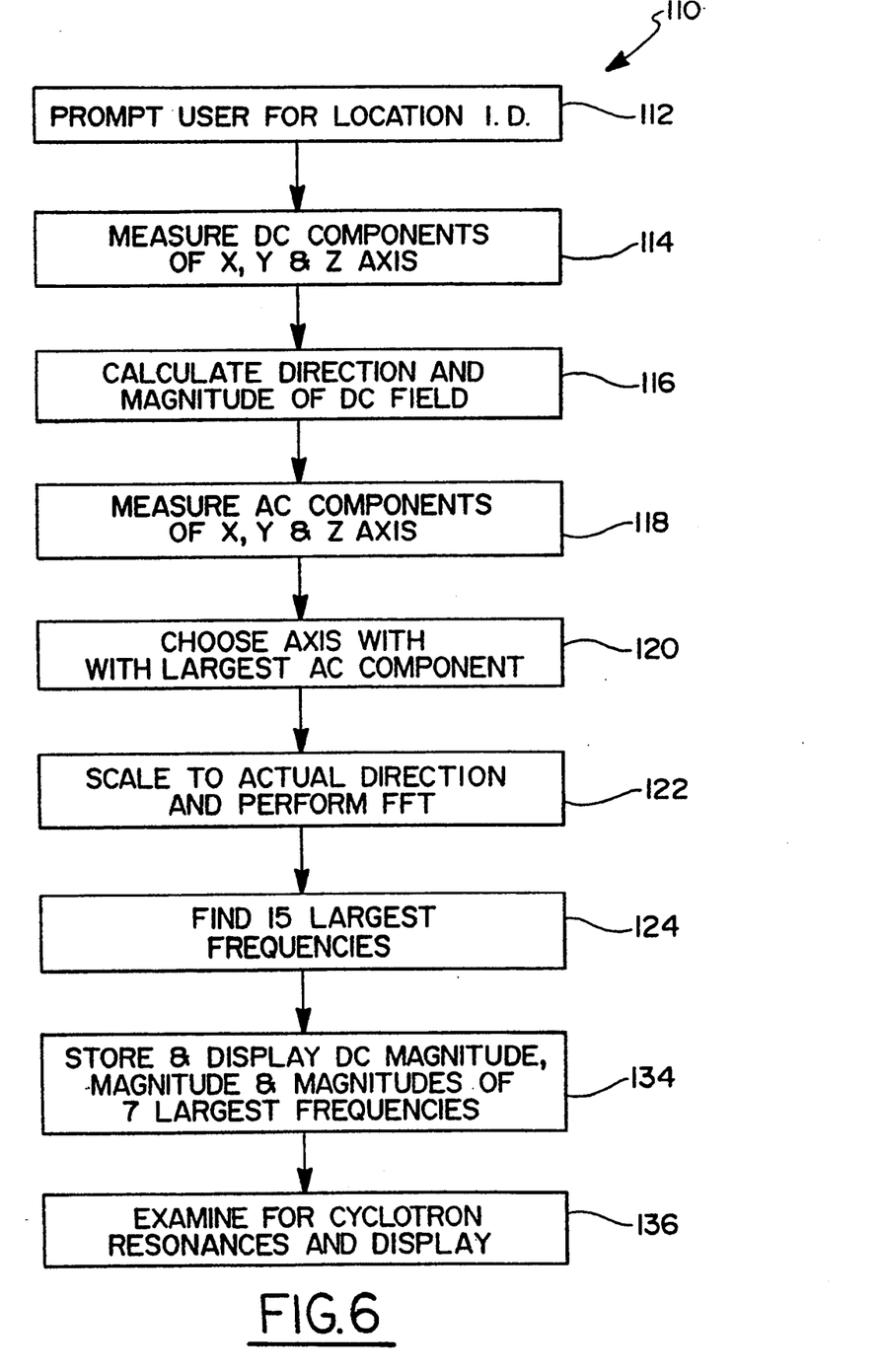
FIG. 6 is a flow chart illustrating the sequence of steps associated with the "take measurements" step of the flow chart shown in FIG. 4.

To appreciate and to understand the operational steps involved in the "take measurements" step 104, reference is now made to flow chart 110, of FIG. 6. As shown, step 104 begins with an initial step 112, in which microcontroller 29 directs device 82 or computer 52 to prompt a user to input a data identification number. Upon a proper identification input, step 112 is followed by step 114, in which microcontroller 29 measures the direct current or non-time varying (i.e. "dc") components of the three magnetic field amplitude signals 56 which will be the sum of the fields emanating along the axes from both dc (predominately geomagnetic) and any other dc magnetic field sources. Microcontroller 29 uses these components to calculate the direction and amplitude or magnitude of the total static, i.e., the dc field resulting from all sources (step 116).

Step 116 is then followed by step 118 in which the alternating current (i.e. time varying or ac) components uniquely associated with the fields along each axes are measured by microcontroller 29. The dc source fields may be first filtered out. Based on the signals received from magnetometer 12, microcontroller 29 in one embodiment chooses the signal having the largest amplitude, i.e. either x, y or z, and performs further analysis only on that signal. Alternatively, all three signals may be analyzed. (Also, where the ac amplitude is varying, it may be necessary to determine an average value). Thus, as stated, step 118 may be followed by step 120, in which microcontroller 29 chooses the one alternating current component signal with the largest alternating current amplitude or magnitude. Should there be two components having substantially equal values, microcontroller 29 arbitrarily selects one of them.

Step 121 follows step 120 and, in this step, microcontroller 29, after ac and dc fields have been measured, calculates the component of the dc field that is in the direction of, that is parallel to, the ac field vector. To this end, microcontroller 29 takes the measured ac and dc magnitudes and the declination angles theta and phi, which are standard angles in a spherical system of coordinates, and calculates the ac vector and the dc vector in a standard x, y, z coordinate system. Then it calculates the vector dot product of the two vectors and divides the result by the magnitude of the ac magnetic field. It is this step that yields the component of the dc field that is in the direction of the ac magnetic field.

Step 121 is followed by step 122 where microcontroller 29 performs a frequency transformation operation (on the largest alternating current signal component or on all 3 components X, Y and Z). This transformation is effective to obtain the fundamental frequency and the lower order frequency harmonic components comprising the selected ac field. In the preferred embodiment of this invention, this frequency transformation is achieved by means of a Fast Fourier Transform (FFT). However, it should be apparent to one of ordinary skill in the art that any other frequency transformation may be used, such as the typical and known "Z" transform. Moreover, the received ac signals are initially directionally scaled, in a conventional manner, before this transformation is accomplished. Methods for determining the fundamental frequency and the lower order harmonics using Fast Fourier Transform are well known in the art.

Step 124 follows step 122, and in this step, microcontroller 29 finds or identifies the largest fifteen frequency harmonic components, associated with the signature generated by the Fast Fourier Transform operation. It should be apparent to one of ordinary skill in the art, that while fifteen frequencies are used in the preferred embodiment of the invention, a different number of frequencies may alternatively be used. A representative Fast Fourier Transform frequency signature is shown in graph 126, of FIG. 7.

Figure 7:
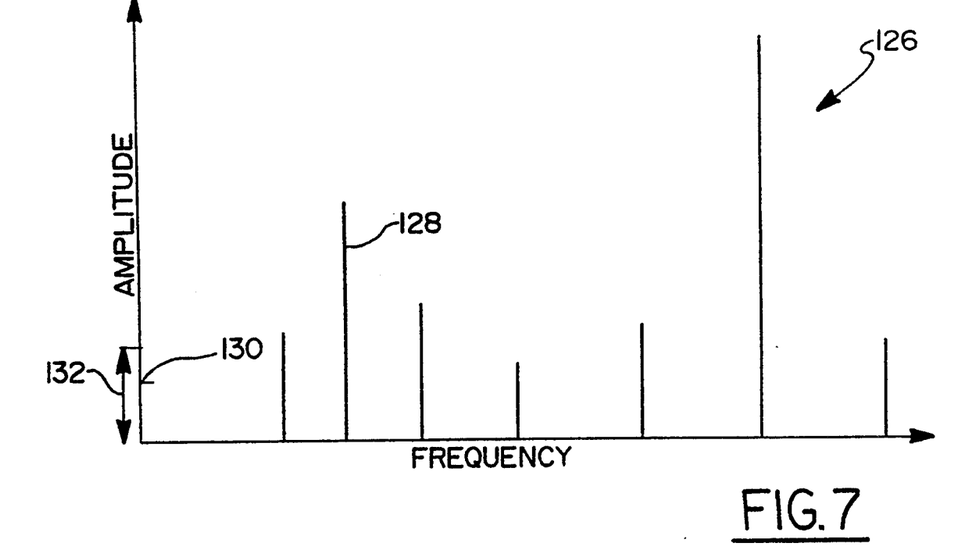
FIG. 7 is a graph illustrating a typical Fourier harmonic signal signature, associated with the signal emanating from the three axis magnetometer shown in FIG. 1.

Specifically, and as will be appreciated by those of ordinary skill in the art, the alternating current signal or ac magnetic field component is represented by frequency harmonic pulses 128, of varying amplitude and frequency. Moreover, and as will be further appreciated by one of ordinary skill in the art, the direct current component is associated with pulse 130, having a certain amplitude 132 and a frequency of substantially zero. Moreover, the magnitude 132 and spatial direction angles of the direct current pulse 130 and the magnitudes of the seven largest frequencies 128 are stored within memory 76 and displayed by device 84 and/or computer 52, in step 134. Step 136 follows step 134, and in this step microcontroller 29 examines the fifteen frequency harmonic signature components 128 and the fundamental frequency for a cyclotron resonance "condition".

In step 136 of the preferred embodiment of this invention, microcontroller 29 is adapted to determine whether frequency harmonic components 128, and/or the fundamental frequency, have a frequency which, based on the measured, and then calculated in step 121, dc field-strength, is substantially equal to the cyclotron resonance frequency of certain biologically important ions such as $H^+$, $Lt^+$, $Mg^{++}$, $Ca^{++}$, $Na^+$, $Cl^-$, $K^+$, and $HCO^-$ ions, or is a third, fifth, or fifteenth multiple of these frequencies.

Specifically, and as known to one of ordinary skill in the art, cyclotron resonance frequency may generally be described by the following equation:

$$f_c = (\tfrac{1}{2}\pi)\,(q/m)\,(Bdc_{calc})\,(N)$$

where:

N = a positive number;

$f_c$ = frequency of the harmonic component;

(q/m) = characteristic change-to-mass ratio associated with ions such as calcium, potassium, and magnesium; and ($Bdc_{calc}$) = calculated direct current magnetic field component amplitude.

Therefore, in one embodiment in step 136, microcontroller 29 solves the equation for "N", by dividing the frequency of each of the frequency components 128 (and the fundamental frequency) ("$f_c$") by the product of ($\tfrac{1}{2}\pi$); the charge-to-mass ratio associated with each of the selected ions; and the "dc" measured and then calculated magnetic field, in order to determine if the frequency of any of the components 128 (or fundamental frequency) is substantially equal to a predetermined multiple of the cyclotron resonance frequency of the ions. As is known to those of ordinary skill in the art, the characteristic charge-to-mass ratio for the calcium ion is approximately 76.6, and is approximately 39.8 for the potassium ion. Moreover, this ratio is approximately 126.6 for the magnesium ion.

In one embodiment, if "N" is found to equal 1, 3, 5, or 15, (or within ±five percent of this value) and the amplitude of any of these frequency signature components 128 exceeds a level set by the user, such as 2 milligauss, a potential health hazard may exist. Microcontroller 29 is adapted to output a signal onto bus 67, effective to display a warning signal upon device 84 and/or computer 52. Moreover, microcontroller 29, in step 136, further examines the amplitude of each signal 128, 130 and outputs a warning signal onto bus 78, if N=1, 3, 5 or 15 and if the ac amplitude exceeds 2 milligauss. If either of these two conditions is not met, the warning signal is not produced. In this manner, it should further be apparent to one of ordinary skill in the art that a user of analyzer 10 may be readily warned if a potential magnetic field health risk exists. All field values are stored in the memory as well so the user can download them at a later date and do other calculations with the measured values. The result of the 1-15/0 output is a "resonance map" consisting of zeros and the numbers 1, 3, 5, and 15. This can be plotted in a three dimensional contour plot that clearly shows the resonances for each of the three ions and each of the measured frequency components. Since all of this is done at each place where a measurement is taken, the magnetometer can create a resonance screening of an entire area very rapidly.

In another aspect and method, the present invention can be described as a magnetic field analyzer 10 for determining the presence of potentially hazardous magnetic fields in a pre-selected area which includes the steps of spatial and magnetic orienting analyzer 10, with the magnetometer function of analyzer 10; determining the B field along an axis in the area, where the B field is the total field resulting from both ac and dc magnetic-field-emanating sources, with calculating a dc component corresponding to a dc field component directionally coinciding with said ac field component; calculating a fundamental resonance frequency value based on the measured and calculated dc B field magnitude for biologically important ions such as calcium, magnesium and potassium, and calculating selected harmonics for these biologically important ions, preferably the 3, 5 and 15 harmonics; storing this data in data storage means in association with analyzer 10; by way of Fast Fourier Transform, or other equivalent means, determining the fundamental frequency using the dc magnetic field sensed along the axis, and then calculated, and the 15 largest harmonic frequencies of the sensed field; comparing the fundamental and harmonic frequencies of the sensed magnetic field with the stored frequency data for the biologically significant ions which was calculated based on the measured dc B field value and stored in the storage means; and providing a readout on analyzer 10 of information on the fundamental and/or those harmonic frequencies of the measured field which are within a preselected percentage of the stored value for specific ion resonances, for example, within ±5%.

It is to be understood that the invention is not limited to the exact construction or method illustrated and described above, but that various changes and modifications may be made without departing from the spirit and scope of the invention, as defined in the following claims.

What is claimed is:

1. A portable magnetic field analyzer comprising:

a three-axis magnetometer adapted to measure an ambient magnetic field having components from both ac and dc magnetic field sources and to output a measurement signal having a plurality of frequency harmonic components;

an analog-to-digital converter for digitizing said measurement signal;

memory storage means for storing at least one cyclotron resonance frequency;

microcontroller means, connected to said memory storage means and adapted to receive said digitized output signal for defining a dc component directionally coinciding with said ac component, processing said digitized signal in view of said directionally coinciding dc component by fast Fourier transform and for comparing said digital output signal with said at least one cyclotron resonance frequency; and means for visually displaying information relating to said comparison.

2. The magnetic field analyzer of claim 1 further comprising:

input means, connected to said microcontroller, for selectively and uniquely associating said measurement signal with a unique identification tag.

3. The magnetic field analyzer of claim 1, further comprising means for spatial and magnetic orientation of said magnetometer.

4. The magnetic field analyzer of claim 1, wherein said at least one cyclotron resonance frequency comprises the cyclotron resonance frequency of the calcium ion.

5. The magnetic field analyzer of claim 1, wherein said at least one cyclotron resonance frequency comprises the cyclotron resonance frequency of the potassium ion.

6. The magnetic field analyzer of claim 1, wherein said at least one cyclotron resonance frequency comprises the cyclotron resonance frequency of the magnesium ion.

7. A portable magnetic field analyzer comprising:
a three-axis magnetometer adapted to measure a magnetic field having components from both ac and dc magnetic field sources and to output a measurement signal representing an amplitude of said measured magnetic field;
an analog-to-digital convertor for digitizing said measurement signal;
memory storage means for storing the characteristic charge-to-mass ratio of at least one preselected ion;
microcontroller means, connected to said memory storage means and adapted to receive said digital output signal, for deriving a dc component from said digitized output signal to provide a modified dc component corresponding to a dc field component directionally coinciding with said ac field component, performing a frequency transformation operation upon said digitized output electrical signal in view of said modified dc component by fast Fourier transform, effective to produce a first signal indicative of an amplitude of said modified direct current component of said output electrical signal, and a second signal indicative of an amplitude and a frequency of an alternating current fundamental component of said output electrical signal and for creating a number by dividing said second fundamental signal by the product of said modified direct current component and said stored charge-to-mass ratio of said at least one preselected ion, and for comparing said number with at least one preselected number, and for outputting a signal when said number is substantially equal to said preselected number; and
means for visually displaying information relating to said comparison.

8. The magnetic field analyzer of claim 7, wherein said at least one preselected ion comprises potassium.

9. The magnetic field analyzer of claim 7, wherein said at least one preselected ion comprises calcium.

10. The magnetic field analyzer of claim 7, wherein said at least one preselected ion comprises magnesium.

11. The magnetic field analyzer of claim 7, further comprising means for spatial and magnetic orientation of said magnetometer.

12. The magnetic field analyzer of claim 7, further comprising input means, connected to said microcontroller, for selectively and uniquely associating said measurement signal with a unique identification tag.

13. A portable magnetic field analyzer, adapted to measure a magnetic field having components from both ac and dc magnetic field sources and to selectively generate a warning signal, adapted to indicate a potential magnetic field health risk, said analyzer comprising:
a three-axis magnetometer adapted to measure said magnetic field and to output an electrical signal representing an amplitude of said measured magnetic field;
means for spatial and magnetic orientation of said magnetometer;
an analog-to-digital convertor for digitizing said output signal;
microcontroller means, electrically coupled to said magnetometer and adapted to receive said digitized output signal, for deriving a dc component from said digitized output signal to provide a modified dc component corresponding to a dc field component directionally coinciding with said ac field component, performing a frequency transformation operation upon said digitized output electrical signal in view of said modified dc component by fast Fourier transform, effective to produce a first signal indicative of an amplitude of said modified direct current component, and a signal indicative of a fundamental frequency and an amplitude of an alternating current harmonic component of said digitized output signal, and for comparing each of said first and fundamental signals with a preselected value, and for selectively outputting a signal based upon said comparison, and for comparing said fundamental signal with at least one preselected cell proliferation frequency, and for selectively outputting a second signal when said fundamental signal equals said at least one preselected cell proliferation frequency, whereby said produced first and second signals cooperate to provide a warning of a potential magnetic field health risk; and
means for visually displaying information relating to said comparison.

14. The magnetic field analyzer of claim 13, wherein said certain preselected cell proliferation frequencies comprise the cyclotron resonance frequency of a potassium ion and the cyclotron resonance frequency of a calcium ion and the cyclotron resonance frequency of a magnesium ion.

15. A portable magnetic field analyzer consisting essentially of:
means for measuring the frequency and magnitude of a magnetic field along three axes, where the magnetic field is produced by both dc and ac sources, and where said dc source includes the geomagnetic field, wherein said measuring means outputs a signal containing field magnitude and frequency information;
means for spatial and magnetic orienting said measuring means;
an analog-to-digital convertor for digitizing said output signal;
means for storing information on biological ions;
microcontroller means for deriving a dc component from said digitized output signal to provide a modified dc component corresponding to a dc field component directionally coinciding with said ac field component, processing said digitized output signal in view of said modified dc component by fast Fourier transform for comparing at least a portion of said magnitude and frequency information with information on biological ions from said storage means and for determining whether the signal from said measuring means indicates that the measured magnetic field has a value within a preselected percentage of the cyclotron resonance conditions for said biological ions;
notification means for notifying a user of said magnetic fields analyzer that the measured field signal has a value within said preselected percentage of said cyclotron resonance condition for said biological ions; and power means for supplying power to said measuring, converting, storing, microcontroller and notification means.

16. A method of analyzing a magnetic field comprising the steps of:
   measuring an ambient magnetic field having components from both ac and dc magnetic field sources with a portable three-axis magnetometer to output a measurement signal having a dc signal and a plurality of frequency harmonic components;
   analog-to-digital converting said output signal for digitizing thereof;
   storing at least one cyclotron resonance frequency in a memory storage means;
   deriving a dc component from said digitized output signal to provide a modified dc component corresponding to a dc field component directionally coinciding with said ac field component;
   processing said digitized output signal in view of said modified dc component by fast Fourier transform and comparing said measurement signal to said at least one cyclotron resonance frequency with a microcontroller means connected to said memory storage means and adapted to receive said digitized output signal; and
   notifying a user of the results of said comparison.

17. The method of analyzing a magnetic field of claim 16, further comprising preliminary placing said magnetometer into a preselected position as to height, horizontal level and magnetic orientation.

18. The method of analyzing a magnetic field of claim 16, wherein said notifying said user is in a form selected from the group consisting of visual, written and audible form.

19. The method of analyzing a magnetic field of claim 16, further comprising repeating of said steps with said measuring using the same spatial and magnetic orientation.

20. A method of analyzing a magnetic field comprising the steps of:
   spatial and magnetic orienting a means for said analysis;
   measuring an ambient magnetic field having components from both ac and dc magnetic field sources with a portable three-axis magnetometer to output a measurement signal having a dc signal and a plurality of frequency harmonic components;
   analog-to-digital converting said output signal for digitizing thereof;
   storing at least one cyclotron resonance frequency in a memory storage means;
   deriving a dc component from said digitized output signal to provide a modified dc component corresponding to a dc field component directionally coinciding with said ac field component;
   processing said digitized output signal in view of said modified dc component by fast Fourier transform and comparing said measurement signal to said at least one cyclotron resonance frequency with a microcontroller means connected to said memory storage means and adapted to receive said digitized output signal; and
   notifying a user of the results of said comparison.

* * * * *